United States Patent [19]

Hooper et al.

[11] Patent Number: 5,257,622
[45] Date of Patent: Nov. 2, 1993

[54] LOCKING CONNECTOR FOR IMPLANTABLE DEVICE

[75] Inventors: William J. Hooper, Lake Elmo; John E. Nicholson, Blaine, both of Minn.

[73] Assignee: Medtronic, Inc., Minneapolis, Minn.

[21] Appl. No.: 762,273

[22] Filed: Sep. 19, 1991

[51] Int. Cl.⁵ ............................................. A61N 1/375
[52] U.S. Cl. ................................................... 607/37
[58] Field of Search ........................................ 128/419 P

[56] References Cited

U.S. PATENT DOCUMENTS

| | | | |
|---|---|---|---|
| 4,072,154 | 2/1978 | Anderson | 128/419 |
| 4,105,037 | 8/1978 | Richter et al. | 128/419 |
| 4,112,953 | 9/1978 | Shanker et al. | 128/419 |
| 4,180,078 | 12/1979 | Anderson | 128/419 |
| 4,226,244 | 10/1980 | Coury et al. | 128/419 |
| 4,248,237 | 2/1981 | Kenny | 128/419 P |
| 4,262,673 | 4/1981 | Kinney et al. | 128/419 |
| 4,301,805 | 11/1981 | Peers-Trevarton et al. | 128/419 |
| 4,310,001 | 1/1982 | Comben | 128/419 |
| 4,469,104 | 9/1984 | Peers-Trevarton | 128/419 |
| 4,479,489 | 10/1984 | Tucci | 128/419 |
| 4,540,236 | 9/1985 | Peers-Trevarton | 339/45 |
| 4,603,696 | 8/1986 | Cross, Jr. | 128/419 |
| 4,712,557 | 12/1987 | Harris | 128/419 |
| 4,715,380 | 12/1987 | Harris | 128/419 |
| 4,764,132 | 8/1988 | Stutz, Jr. | 439/810 |
| 4,799,902 | 1/1989 | Laudig et al. | 493/585 |
| 4,848,346 | 7/1989 | Crawford | 128/419 |
| 4,860,750 | 8/1989 | Frey et al. | 128/419 |
| 4,907,592 | 3/1990 | Harper | 128/419 |
| 4,913,147 | 4/1990 | Fahlstrom et al. | 128/419 P |
| 4,934,366 | 6/1990 | Truex et al. | 128/419 P |
| 4,934,367 | 6/1990 | Daglow et al. | 439/527 |
| 5,070,605 | 12/1991 | Daglow et al. | 128/419 P |

*Primary Examiner*—William E. Kamm
*Assistant Examiner*—Scott M. Getzow
*Attorney, Agent, or Firm*—Harold R. Patton; Gregory P. Gadson

[57] ABSTRACT

A conical annulus formed on a pacer lead body engages a deformable retention ring formed on the connector block to hold the lead in the pacer.

11 Claims, 4 Drawing Sheets

LOCKING CONNECTOR FOR IMPLANTABLE DEVICE

BACKGROUND OF THE INVENTION

1. Field of the Invention

This invention relates generally to implantable medical devices, and more particularly to apparatus for connecting the lead or catheter to the implantable device.

2. Description of the Prior Art

At present, the most widely used implantable medical device is the cardiac pacemaker. The modern pacer system includes a pacing lead and an implantable pulse generator or pacemaker.

Pacers, which provide therapeutic stimulation to the heart to correct conduction disorders, have been a treatment of choice since the early 1960's. The earliest pacemakers included a battery-powered pulse generator which was physically connected to an integral catheter or lead system. In use, the electrodes of the lead system would be sutured directly to the myocardium of the heart while the pulse generator would be implanted subcutaneously under the skin. This early pacemaking system utilized Dow Corning Silastic rubber as the principle covering material to ensure biocompatibility, while the electronic portion of the pacer was imbedded or "potted" in Scotch Cast 5 epoxy which has been manufactured by the 3M Company. Electrode areas were typically made from stainless steel or platinum-iridium alloy.

Improvements in the delivery of pacer therapy have resulted in the modern form of pacer which includes a hermetically sealed pulse generator which is readily connected to a separate lead system.

In general, the connection between the pacer or pulse generator and the lead is made in a, so called "connector block" which is attached to body of the pacer. This connector block is typically formed from transparent plastic and it contains structures to facilitate both, electrical connection and mechanical coupling between the implanted lead system and the pacer. Feed-throughs, located in part in the connector block, provide electrical connection between the electronic components within the pacer and the connector block contacts.

In the prior art, set screws and cross-drilled contact blocks have been used to couple the lead to the feed through. This simple expedient permits good electrical and mechanical contact. However, unless certain precautions are taken, it is possible to over, or under, tighten the set screw which can lead to poor coupling. One example of a particularly successful set screw system of the type discussed above, is known from U.S. Pat. No. 4,226,244 to Coury et al.

A number of alternatives to the manually tightened set screw have been proposed. For example, U.S. Pat. No. 4,540,236 to Peers-Trevarton teaches a "push-button" style release structure; U.S. Pat. No. 4,712,557 teaches inter alia, a wedge member to lock the lead in the pacer; and, U. S. Pat. No. 4,105,037 teaches a bayonet type of attachment between the lead and the pacer.

SUMMARY OF THE INVENTION

In contrast to the prior art, the present invention relies upon a relatively rigid lock collar formed on the lead or catheter, which cooperates with a deformable retention ring on the connector block.

These two elements cooperate together to provide mechanical coupling and retention between the lead and the connector block. Preferably, the lock collar formed on the lead body, has an asymmetrical contour, or shoulder, so that the connection or insertion force is small and the removal force is large. The deformable retention ring on the pacemaker's connector block has a first relaxed position corresponding to a "locked" position, and a second deformed state corresponding to a "released" position. This deformable retention ring permits the stress free release of the lead should repositioning of the pacemaker or replacement of the pacemaker become necessary.

BRIEF DESCRIPTION OF THE DRAWINGS

Throughout the several views of the drawing, identical reference numbers indicate identical structure, wherein.

DETAILED DESCRIPTION OF THE PREFERRED EMBODIMENT

Figure 1:
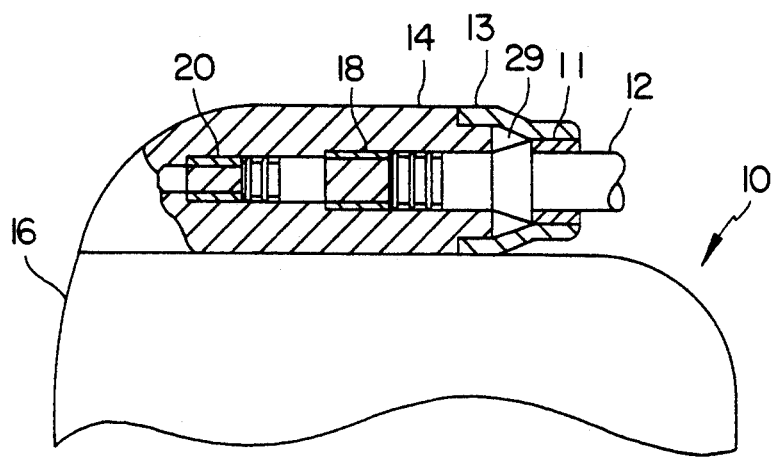
FIG. 1 is an assembly view of a pacemaker and lead according to a first embodiment of the invention.

FIG. 1 depicts the assembly view of the pulse generator 10 and the associated lead 12. In use, the pulse generator 10 is implanted subcutaneously and the lead system 12 is passed transvenously into the heart. The physician connects the lead to the pulse generator and then closes the incision to complete the implantation.

In the present invention, the preferred coupling process involves insertion of the proximal end of the lead 12 into the connector block 14 of the implantable pulse generator 10, after deforming the retention ring 11, and sliding the lead into the pacer until the lock collar 29 is aligned with the retention ring 11.

The electrical contacts 18 and 20 located in the connector block connect the electronics contained within the body 16 of the implantable pulse generator 10, with electrodes located on the distal tip of the lead 12. A conformal boot 13, preferably of Silastic, surrounds the locking ring 11 region to prevent entry of body fluids into the connector block structures of the pacer.

Figure 2:
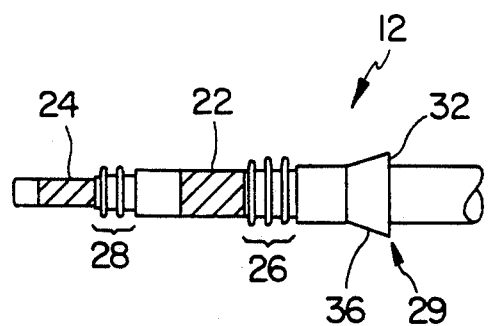
FIG. 2 is an elevational view of the lead portion of the first embodiment of the invention.
Figure 5:
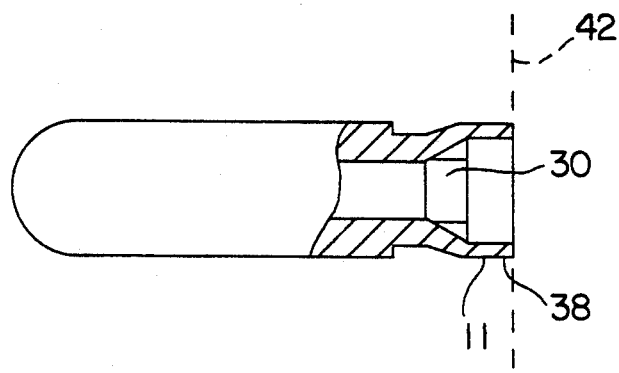
FIG. 5 is a schematic cross-sectional top view of the connector block of the first embodiment of the invention.

FIG. 2 shows the proximal end of the lead 12 in isolation. The electrode contact surfaces 22 and 24 at this end of the electrode body cooperate, and mate with, the pacer electrode contacts 18 and 20.

This stepped annular electrode structure, depicted in FIG. 2 is referred to in the industry as an "inline" construction, since the annular electrode contacts are concentric and therefore in the same line. It should be clear that the retention and lock features are independent of the proximal lead construction and can be implemented in conventional bifurcated or other non-inline lead bodies as well.

As shown in FIG. 2, two sets of integral sealing rings 26 and 28 operate to isolate the electrodes 22 and 24 from each other and operate to exclude moisture and other body fluids from the interior of the connector block.

Figure 3:
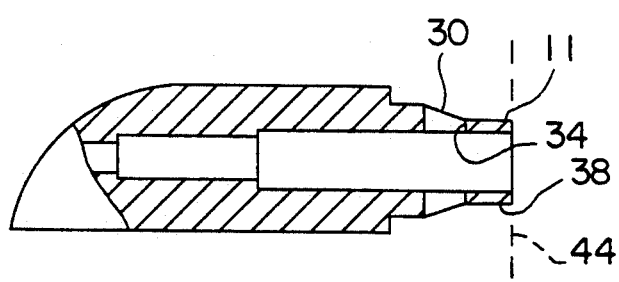
FIG. 3 is a schematic cross-sectional side view of the connector block of the first embodiment of the invention.

Mechanical connection between the lead and pacer is accomplished by cooperation between the conical, annular, lock collar 29 formed o the lead and the apertures or window 30 formed in the retention ring 11 best seen in FIG. 3. As shown, it is preferred to form the deformable retention ring 11 as a unitary part of the connector block 14.

The preferred lock collar is conical and is best seen in FIG. 2. The conical annulus has a major diameter and a minor diameter. As shown in the drawing, the major diameter is larger than the diameter of the lead body while the minor diameter is substantially the same as the diameter of the lead body. In most pacing type applications the minor diameter will be closest to the proximal end of the lead. The major diameter surface, of the annulus, forms the riser portion 32 of the lock collar, while the conical surface forms the ramp surface 36 of the lock collar. Turning to FIG. 3, it can be seen that the riser portion 32 abuts the wall 34 of the aperture or window 30 in the retention ring 11. The abutment between the riser surface 32 and the wall 34 of the window holds the shoulder of the lock collar in the retention ring 11.

If the lead is pushed into the pacer connector block the ramp surface 36 of the lock collar 29 can gradually deflect the retention ring 11 upon entry. This wedging action can provide a relatively low insertion force for entry of the lead 12 into the connector block 14. The acute angle or shoulder formed at the intersection of the ramp surface 36 and the riser surface 32 enters the window 30 and provides a relatively high "forced" removal force, as best seen in FIG. 1.

It is preferred to have sufficient compliance in the retention ring 11 and lock collar to permit the "forced" removal of the lead from the connector block without permanent damage to either the pacer or the pacer lead. However, in operation, it is preferred that the user manually deform the retention ring 11 to permit stress free insertion or removal of the lead.

Figure 4:
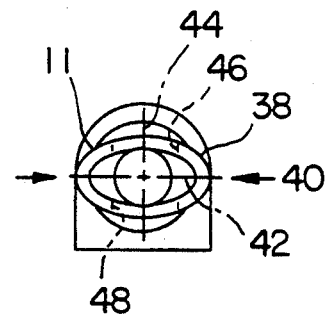
FIG. 4 is an end view of the connector block of the first embodiment of the invention.

In general, it is preferred to have the user insert lead body into the connector block by "squeezing" the elliptical form exterior actuation surface 38 of the retention ring as indicated by force vector 40 in FIG. 4. The preferred elliptical shape of this actuation surface is best seen in the view of FIG. 4, where the major axis 42 and minor axis 44 of the ellipse are identified. "Squeezing" actuation surface 38 deforms the retention ring 11 into an approximately circular cross-section; and permits the unobstructed entry of the lead into the connector block 14. With the lead fully inserted, the elliptical ring 38 is released and it returns to the original or relaxed position as depicted in FIG. 4, thus trapping the lock collar shoulder 29 within the complimentary lock window structures 30.

Preferably, removal of the lead is accomplished by "pinching" the actuation surface by applying a force along the major axis of the ring 42 as indicated by vector 40 in FIG. 4.

In summary, to minimize stress on the lead and connector, it is preferred that the user pinch the elliptical ring along its major axis during both insertion and removal.

Although the preferred shape of the actuator surface 38 is an ellipsoid having a major axis 42 and a minor axis 44, other shapes are suitable. Likewise, it is preferred to have a pair of complimentary apertures or windows 46 and 48, sized to accept the shoulder of the lock collar into engagement. However, larger and smaller apertures are usable variations on the disclosed preferred structure. The number of windows may be varied as well. It is also possible but difficult to mold the windows with a membrane over there outer surface.

Figure 6:
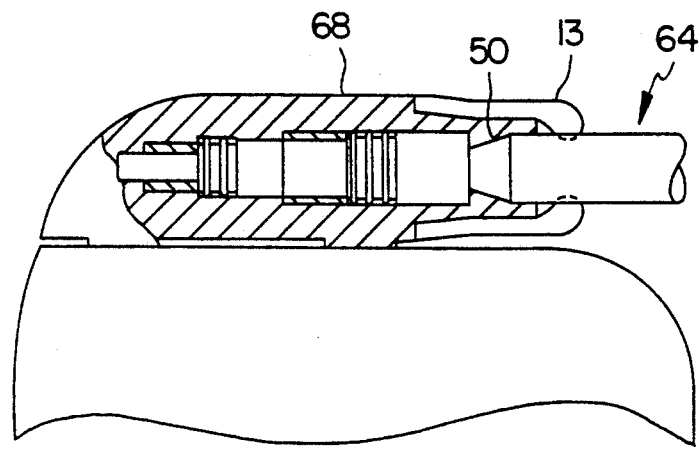
FIG. 6 is an assembly view of a second embodiment of the invention.
Figure 7:
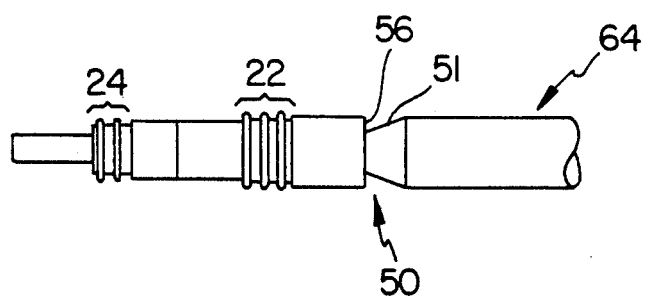
FIG. 7 is an elevational view of the lead portion of the second embodiment of the invention.
Figure 9:
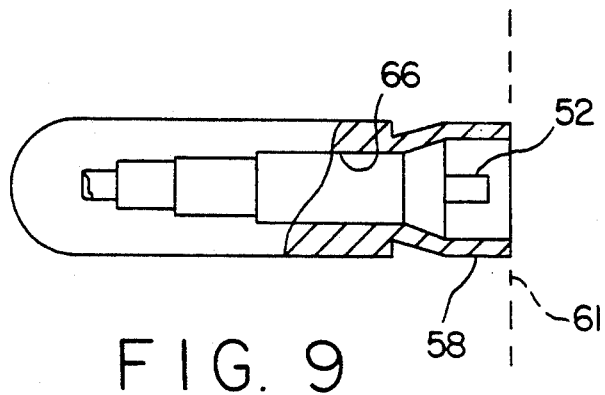
FIG. 9 is a schematic cross-section top view of the connector block of the second embodiment of the invention.
Figure 8:
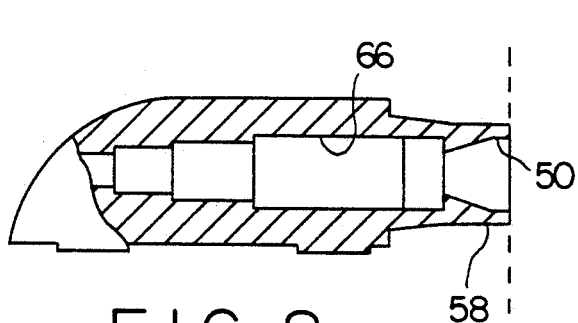
FIG. 8 is a schematic cross-section side view of the connector block elevation of a second embodiment of the invention.

FIG. 6 shows a complimentary embodiment of the invention in which the lock collar 50 has a reduced diameter. Here, the major diameter of the conical annulus is substantially the same size as the lead body, while the minor diameter is smaller than the lead body diameter. For most pacing type applications the minor diameter will be the closest to the proximal end.

Figure 10:
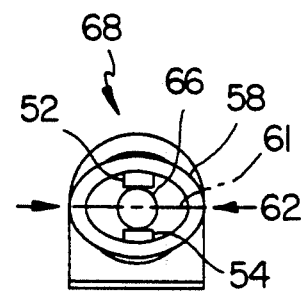
FIG. 10 is an end view of the connector block of the second embodiment of the invention.

This embodiment can be used to reduce the overall size of the connector block. In this embodiment, a pair of lock features, block 52 and block 54 as shown on FIG. 10 engage and abut the riser surface 56 of the lock collar 50, as best seen in FIG. 6. A disadvantage of this embodiment is that it requires the user to squeeze the deformable retention ring 58 along its major axis 61 by applying force as indicated by vector 62 to permit entry of the lead body 64 into lead reception aperture 66 of the connector block 68. Failure to deform the ring prior to insertion of the lead will cause the lock features 52 and 54 to engage the sealing rings 24 and 22, which can potentially damage them. For this reason, the first embodiment of the invention is more tolerant of misuse by the user.

Figure 11:
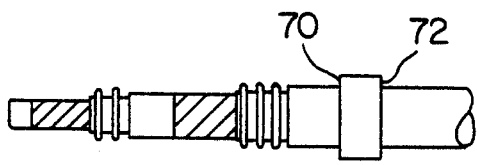
FIG. 11 is a elevational view of a lead depicting a symmetrical lock collar.

In each of the illustrative embodiments, the locking collar portion 50 of the lead 64 is asymmetric, and has ramp-like surface 51 as well as a riser-like 56 surface. The asymmetry provides differing insertion and removal forces. In FIG. 11 there is shown a cylindrical locking ring which has a pair of riser surfaces 70 and 72, which provide the locking action. This variant shows how the shoulder contour of the lock collar can be varied to meet the specific requirement of a particular medical device. The illustrative embodiments of the invention are intended to illustrate the invention, and one of ordinary skill can make numerous modifications to the disclosed structure without departing from the scope and spirit of the claims which are appended as follows.

We claim:

1. Apparatus for coupling a catheter to an implantable medical device comprising:
   a catheter having a substantially cylindrical lead body, said lead body having a body diameter, said lead body having a distal end and having a proximal end;
   said lead body having a lock collar, located proximate said proximal end, said lock collar having an engagement surface;

an implantable medical device having a connector block means, for accepting said proximal end of said catheter;

said connector block means having a deformable retention ring means, said retention ring means having a first relaxed state in which said retention ring means has an axial shape which is different from the axial shape of said lock collar and defined by a major axis and a minor axis, and having a second deformed state in which said retention ring means has an axial shape which is substantially identical to the axial shape of said lock collar, for engaging said engagement surface of said lock collar;

said retention ring means having an engagement wall;

whereby said wall abuts said engagement surface of said lock collar when said wall is aligned with said engagement surface and said retention ring is in said first relaxed state, whereby, said wall releases said engagement surface when said retention ring is in said second deformed state, and whereby, applying a compression force along said major axis reduces stress upon said lead body and said connector block means during coupling and de-coupling.

2. The apparatus of claim 1 wherein said lock collar comprises:
a truncated conical annulus having a major diameter and a minor diameter, said major diameter being larger than said lead body diameter, said minor diameter being substantially equal to said lead body diameter.

3. The apparatus of claim 1 wherein said lock collar comprises:
a truncated conical annulus having a major diameter and a minor diameter, said major diameter being substantially equal to said lead body diameter, said minor diameter being smaller than said lead body diameter.

4. The apparatus of claim 1 wherein said lock collar comprises:
a truncated conical annulus having a major diameter and a minor diameter, said major diameter being larger than said lead body diameter, said minor diameter being substantially equal to said lead body diameter;
said minor diameter located closer to said proximal end of said lead than the location of said major diameter.

5. The apparatus of claim 1 wherein said lock collar comprises:
a truncated conical annulus having a major diameter and a minor diameter, said major diameter being larger than said lead body diameter, said minor diameter being substantially equal to said lead body diameter;
said major diameter located closer to said proximal end of said lead than the location of said minor diameter.

6. The apparatus of claim 1 wherein said lock collar comprises:
a truncated conical annulus having a major diameter and a minor diameter, said major diameter being substantially equal to said lead body diameter, said minor diameter being smaller than said lead body diameter.
said minor diameter located closer to said proximal end of said lead than the location of said major diameter.

7. The apparatus of claim 1 wherein said lock collar comprises:
a truncated conical annulus having a major diameter and a minor diameter, said major diameter being substantially equal to said lead body diameter, said minor diameter being smaller than said lead body diameter.
said major diameter located closer to said proximal end of said lead than the location of said minor diameter.

8. The apparatus of claim 1 wherein said lock collar comprises:
a cylindrical annulus having a diameter larger than said lead body diameter.

9. Apparatus for coupling a catheter to an implantable medical device comprising:
a catheter having a substantially cylindrical lead body, said lead body having a body diameter, said lead body having a distal end and having a proximal end;
said lead body having a lock collar, located proximate said proximal end, said lock collar having an engagement surface and comprising a truncated conical annulus having a major diameter and a minor diameter, said major diameter being substantially equal to said lead body diameter, said minor diameter being smaller than said lead body diameter;
an implantable medical device having a connector block means, for accepting said proximal end of said catheter;
said connector block means having a deformable retention ring means, said retention ring means having a first relaxed state and having a second deformed state, for engaging said engagement surface of said lock collar;
said retention ring means having an engagement wall;
whereby, said wall abuts said engagement surface of said lock collar when said wall is aligned with said engagement surface and said retention ring is in said first relaxed state, and
whereby, said wall releases said engagement surface when said retention ring is in said second deformed state.

10. Apparatus for coupling a catheter to an implantable medical device comprising:
a catheter having a substantially cylindrical lead body, said lead body having a body diameter, said lead body having a distal end and having a proximal end;
said lead body having a lock collar, located proximate said proximal end, said lock collar having an engagement surface and comprising a truncated conical annulus having a major diameter and a minor diameter, said major diameter being substantially equal to said lead body diameter, said minor diameter being smaller than said lead body diameter, and said minor diameter located closer to said proximal end of said lead than the location of said major diameter;
an implantable medical device having a connector block means, for accepting said proximal end of said catheter;
said connector block means having a deformable retention ring means, said retention ring means having a first relaxed state and having a second deformed state, for engaging said engagement surface of said lock collar;

said retention ring means having an engagement wall;

whereby, said wall abuts said engagement surface of said lock collar when said wall is aligned with said engagement surface and said retention ring is in said first relaxed state, and whereby, said wall releases said engagement surface when said retention ring is in said second deformed state.

11. Apparatus for coupling a catheter to an implantable medical device comprising:

a catheter having a substantially cylindrical lead body, said lead body having a body diameter, said lead body having a distal end and having a proximal end;

said lead body having a lock collar, located proximate said proximal end, said lock collar having an engagement surface and comprising a truncated conical annulus having a major diameter and a minor diameter, said major diameter being substantially equal to said lead body diameter, said minor diameter being smaller than said lead body diameter, and said major diameter located closer to said proximal end of said lead than the location of said minor diameter;

an implantable medical device having a connector block means, for accepting said proximal end of said catheter;

said connector block means having a deformable retention ring means, said retention ring means having a first relaxed state and having a second deformed state, for engaging said engagement surface of said lock collar;

said retention ring means having an engagement wall;

whereby, said wall abuts said engagement surface of said lock collar when said wall is aligned with said engagement surface and said retention ring is in said first relaxed state, and whereby, said wall releases said engagement surface when said retention ring is in said second deformed state.

* * * * *